(12) United States Patent
Dong et al.

(10) Patent No.: US 8,404,804 B2
(45) Date of Patent: Mar. 26, 2013

(54) METHODS AND INTERMEDIATES FOR CHEMICAL SYNTHESIS OF POLYPEPTIDES AND PROTEINS

(75) Inventors: Zheng Xin Dong, Holliston, MA (US); John S. Eynon, Bellingham, MA (US)

(73) Assignee: Ipsen Pharma S.A.S., Boulogne (FR)

( * ) Notice: Subject to any disclaimer, the term of this patent is extended or adjusted under 35 U.S.C. 154(b) by 333 days.

(21) Appl. No.: 12/675,777

(22) PCT Filed: Aug. 27, 2008

(86) PCT No.: PCT/US2008/010161
§ 371 (c)(1),
(2), (4) Date: Feb. 27, 2010

(87) PCT Pub. No.: WO2009/032133
PCT Pub. Date: Mar. 12, 2009

(65) Prior Publication Data
US 2010/0234564 A1  Sep. 16, 2010

(51) Int. Cl.
*C07K 1/08* (2006.01)
(52) U.S. Cl. ........................................... 530/333
(58) Field of Classification Search .................. None
See application file for complete search history.

(56) References Cited

U.S. PATENT DOCUMENTS

| 5,110,936 | A | 5/1992 | Poli et al. | |
|---|---|---|---|---|
| 5,786,335 | A | 7/1998 | Cody et al. | |
| 6,310,180 | B1 * | 10/2001 | Tam | 530/339 |
| 7,030,217 | B2 | 4/2006 | Canne et al. | |
| 2010/0204449 | A1 * | 8/2010 | Dong et al. | 530/345 |

FOREIGN PATENT DOCUMENTS

| DE | 4032163 A1 * | 4/1992 |
|---|---|---|
| EP | 0410540 | 7/1990 |
| EP | 1 392 718 | 11/2006 |
| WO | WO02/098902 | 12/2002 |
| WO | WO03/106615 | 12/2003 |
| WO | WO2004/007661 | 1/2004 |

OTHER PUBLICATIONS

Undheim et al., ACTA Chemica Scandinavica 1970, 24, 3129-3133.*
Translation to English of DE4032163 A1, Apr. 1992, Germany, 13 pages.*
Low, D.W. et al., "Total Synthesis of Cytochrome B562 by Native Chemical Ligation Using A Removable Auxiliary", Proc. Natl. Acad. Sci. USA, 2001, 98:6554-6559.*
Howard-Lock, H.E. et al., "Amino-acid zwitterion equilibria: vibrational and nuclear magnetic resonance studies of methyl-substituted thiazolidine-4-carboxylic acids", Can. J. Chem., 1986, 64:1215-1219.
Muir, T.W. et al., "Protein synthesis by chemical ligation of unprotected peptides in aqueous solution", Methods in Enzymology, 1977, 289:266-298.
Tam, J.P. et al, "Methods and strategies of peptide ligation", Biopolymers Peptide Science, 2001, 60:194-205.
Hojo, H. et al., "*N*-Alkyl Cysteine-Assisted Thioesterification of Peptides", Tetrahedron Letters, 2007, 48:25-28.
Inamori, Y. et al, "Synthesis of Methyl and Ethyl 3-Alkylthiazolidine-R®-Carboxylates and Their Roots Inhibition of the Growth of *Brassica campestris*", Bioscience, Biotechnology and Biochemistry, 1994, 58:1150-1152.
Jones, R. E. et al, "Specific *N*-Methylations of HPV-16 E7 Peptides Alter Binding to the Retinoblastoma Suppressor Protein", J. Biological Chem., 1992, 267:908-912.
JP S61-18077, 1986, Abstract Only.

* cited by examiner

*Primary Examiner* — Marcela M Cordero Garcia
*Assistant Examiner* — Kaipeen Yang
(74) *Attorney, Agent, or Firm* — Tony K. Uhm

(57) ABSTRACT

The present invention relates to methods and intermediates for chemical synthesis of polypeptides and proteins, and more particularly to methods and intermediates for chemically ligating a peptide fragment containing N-terminal N-methyl-cysteine (SEQ ID NO: 1) with another peptide fragment having C-terminal thioester to generate a β-(methylamino)-thioester intermediate that spontaneously rearranges to form an amide bond. Furthermore, the invention relates to methods of converting N-methyl-thiazolidine to N-methyl-cysteine (SEQ ID NO: 1) of polypeptides and proteins. The invention also relates to methods of synthesizing peptide-thioester from peptide-acid fluoride.

19 Claims, 3 Drawing Sheets

"pg" stands for protecting group.

METHODS AND INTERMEDIATES FOR CHEMICAL SYNTHESIS OF POLYPEPTIDES AND PROTEINS

This application is a United States national stage filing under 35 U.S.C. §371 of international (PCT) application no. PCT/US2008/010161, filed Aug. 27, 2008, and designating the US, which claims priority to U.S. provisional application No. 60/966,416, filed Aug. 28, 2007.

BACKGROUND OF THE INVENTION

The present invention relates to methods and intermediates for chemical synthesis of polypeptides and proteins, and more particularly to methods and intermediates for chemically ligating a peptide fragment containing N-terminal N-methyl-cysteine (SEQ ID NO:1) with another peptide fragment having C-terminal thioester to generate a β-(methylamino)-thioester intermediate that spontaneously rearranges to form an amide bond. Furthermore, the invention relates to methods of converting N-methyl-thiazolidine to N-methyl-cysteine (SEQ ID NO:1) of polypeptides and proteins. The invention also relates to methods of synthesizing peptide-thioester from peptide-acid fluoride.

Several techniques for chemically synthesizing proteins have been developed. See, e.g., Stewart, J. M. et al., *Solid Phase Peptide Synthesis* (Pierce Chemical Co., 2d ed., 1984), and Bodanszky, M. et al., *The Practice of Peptide Synthesis* (Springer-Verlag, 1984). Among them, native chemical ligation has proven to be one of most useful methods for chemically generating native proteins. However, native chemical ligation is only suitable for the synthesis of polypeptides and proteins having cysteine residue(s), which can be used as the connection point(s) for ligating peptide fragments to form the final target polypeptides and proteins.

To produce polypeptide and protein analogs and derivatives which have improved chemical and biological properties, incorporation of unnatural amino acid residue(s) into specific position(s) inside the polypeptides and proteins is sometimes required. Such analogs and derivatives can have improved chemical stability, improved enzymatic stability, prolonged duration of action in vivo, and enhanced biological activities. One class of such unnatural amino acids is the N-methyl amino acids. The N-methyl amino acids can impose conformational constraint on peptide backbone, block hydrogen bonding sites and potentially protect the peptide bonds against enzymatic cleavage (see, e.g., Haviv, F. et al., *J. Med. Chem.*, 1993, 36:363-369; Failie, D. P., et al., *Curr. Med. Chem.*, 1995, 2:654-686; Miller, S. M., et al., *Drug Dev. Res.*, 1995, 35:20-32; and Schmidt, R., et al., *Int. J. Pept. Protein Res.*, 1995, 46:47-55). N-methyl cysteine (SEQ ID NO:1) is one member of this class of unnatural amino acids. To generate biologically more active, enzymatically more stable protein analogs and derivatives, there is a need to develop a new chemical method to incorporate N-methyl-cysteine (SEQ ID NO:1) residue in any desired position inside of proteins.

SUMMARY OF THE INVENTION

Figure 1:
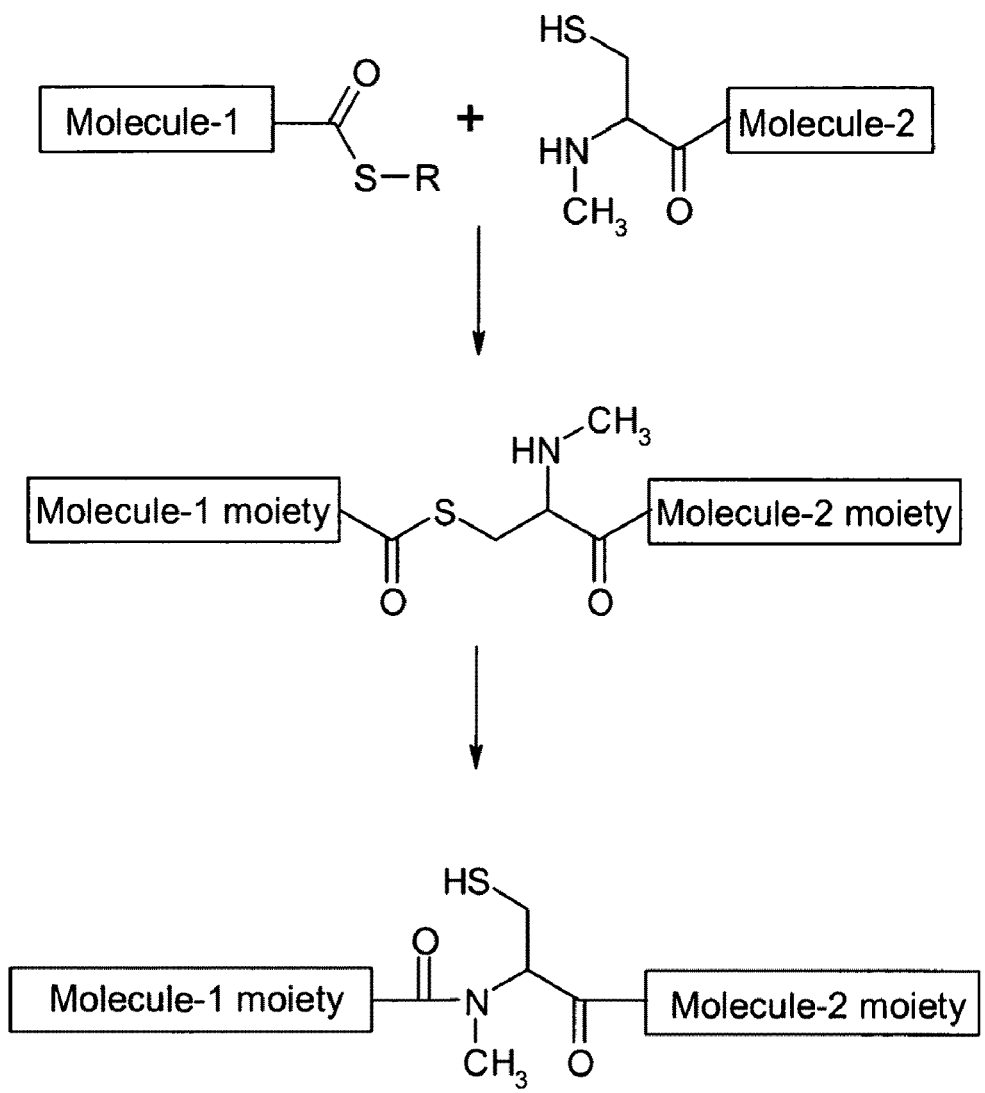
FIG. 1 is an illustration showing a synthetic scheme for forming an amide bond in accordance with one aspect of the present invention.

The present invention is directed to a method of forming an amide bond between two molecules that can be proteins, polypeptides, peptidomimetics, polymers, or any combination thereof. Between these two molecules, one—the "first"—molecule contains a terminal HN-methyl-cysteine (or simply, "N-methyl-cysteine" (SEQ ID NO:1)) residue and the other—the "second"—molecule contains a thioester functional group. During the reaction, the two molecules first connect through a β-(methylamino)-thioester linkage, and then, the β-(methylamino)-thioester linkage spontaneously converts to the final amide bond via an intramolecular rearrangement, as shown in FIG. 1. The resulting final product contains the moieties of the two molecules which are connected through the newly formed amide bond.

Another aspect of the present invention is directed to a ligation reaction which is carried out in a solution or solid phase. The reaction medium may contain thiol catalyst(s). Such thiol catalysts include, but are not limited to, thiophenol, 1-thio-2-nitrophenol, 2-thio-benzoic acid, 2-thio-pyridine, 4-thio-2-pyridinecarboxylic acid, 4-thio-2-nitropyridine, 4-mercaptophenylacetic acid, 2-mercaptoethanesulfonic acid, 3-mercapto-1-propanesulfonic acid, and 2,3-dimercaptopropanesulphonic acid.

Another aspect of the present invention is directed to the conversion of N-methyl-thiazolidine to N-methyl-cysteine (SEQ ID NO:1). For this stepwise ligation, a peptide fragment bearing N-terminal N-methyl-cysteine (SEQ ID NO:1) and C-terminal thioester is needed. However, the conventional thio-protecting groups, such as benzyl for Boc-chemistry and trityl and t-butyl for Fmoc-chemistry, cannot be used to protect the sulfhydryl group of the N-terminal N-methyl-cysteine (SEQ ID NO:1). This is due to the fact that during the final cleavage step, such a conventional protecting group will be removed and a free sulfhydryl group will be generated which will react with the C-terminal thioester to form undesired products.

Figure 2:
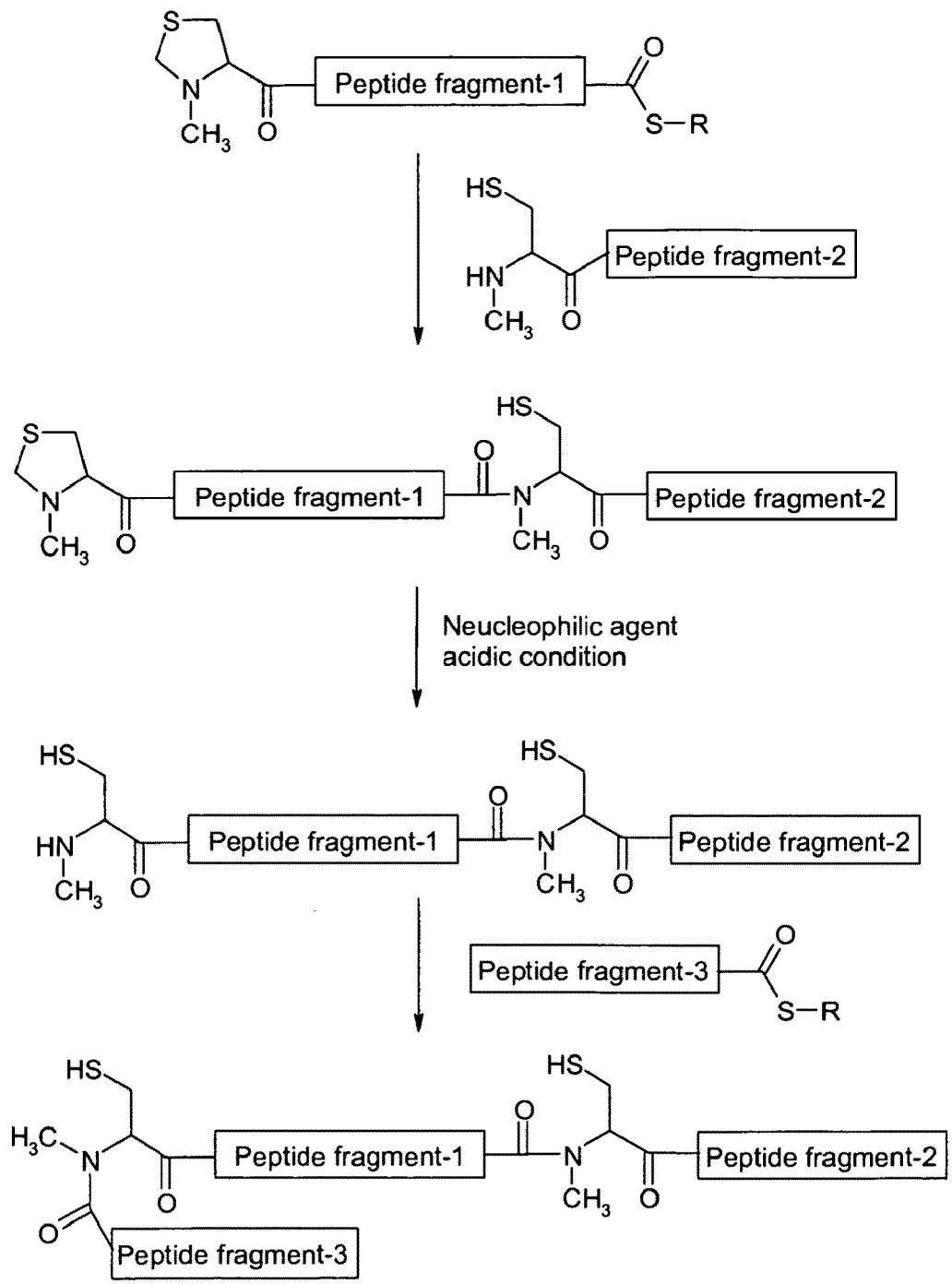
FIG. 2 is an illustration showing a synthetic scheme for protecting N-terminal N-methyl-cysteine (SEQ ID NO:1) in an N-methyl-thiazolidine form during the chemical synthesis of polypeptides and proteins in accordance with one aspect of the present invention.
Figure 3:
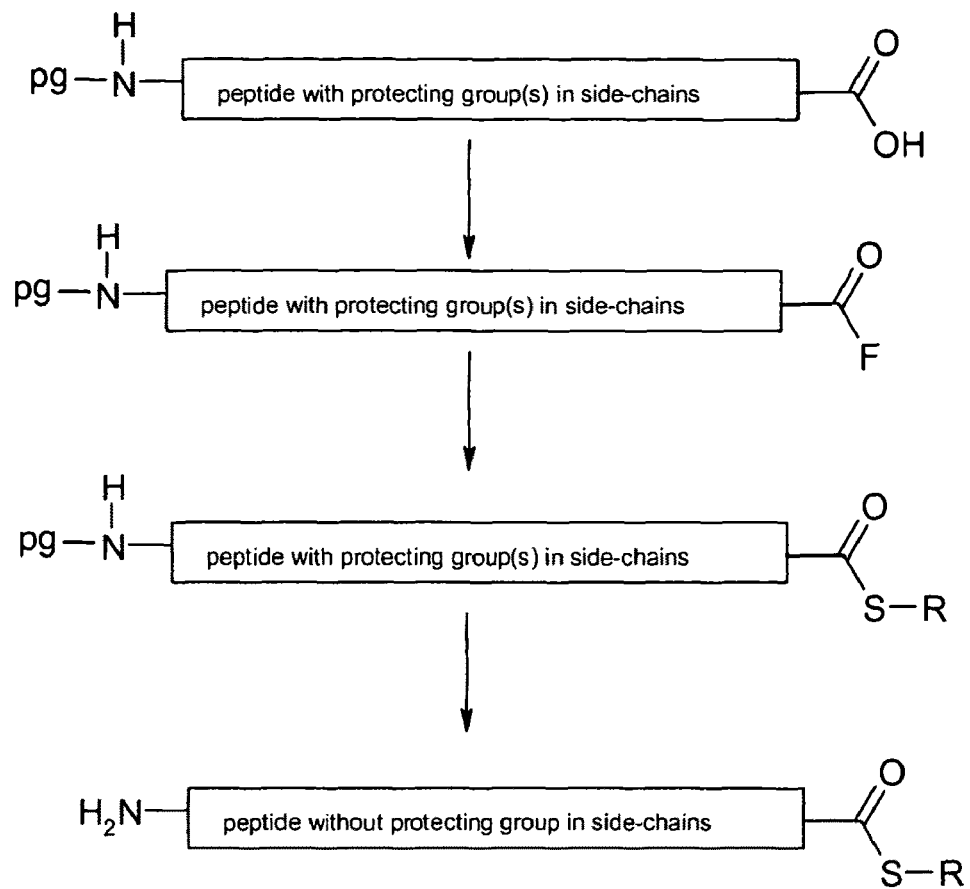
FIG. 3 is an illustration showing a synthetic scheme for synthesizing a peptide-thioester from a protected peptide-acid.

To address this problem, the present invention provides a method for protecting N-terminal N-methyl-cysteine (SEQ ID NO:1) in an N-methyl-thiazolidine form during the chemical synthesis of polypeptides and proteins, as shown in FIG. 2. The N-methyl-thiazolidine will stay intact during the cleavage step and a peptide intermediate containing N-terminal N-methyl-thiazolidine and C-terminal thioester will be generated. This intermediate will be used in the ligation reaction with another peptide fragment containing C-terminal thioester. Only after the ligation reaction, the N-methyl-thiazolidine in the product will be converted to a free N-methyl-cysteine (SEQ ID NO:1) by using a neucleophilic agent under acidic condition, wherein said nucleophilic agent is O-alkylhydroxylamine, and more specifically, wherein said O-alkylhydroxylamine is O-methylhydroxylamine, and wherein said acidic conditions are in the range of pH 2.0 to pH 6.0. The resulting bigger peptide fragment having N-terminal N-methyl-cysteine (SEQ ID NO:1) residue can be used for further ligation step to generate even bigger polypeptides or proteins.

Another aspect of the present invention is directed to methods of synthesizing peptide-thioester from peptide-acid fluoride.

It will be readily apparent to one skilled in the art that other reactants and intermediates may be used, including, but not limited to, N—($C_1$-$C_5$)-cysteine (SEQ ID NO:1), N—($C_1$-$C_5$)-thiazolidine, β-($C_1$-$C_5$ amino)-thioester, and the like.

DETAILED DESCRIPTION OF THE INVENTION

Certain amino acids present in compounds of the invention can be and are represented herein as follows:
Ala or A is alanine,
Arg or R is arginine,
Asn or N is asparagine,
Asp or D is aspartic acid,
Cys or C is cysteine,
Gln or Q is glutamine,
Glu or E is glutamic acid,
Gly or G is glycine,
H is or H is histidine,
Ile or I is isoleucine,
Leu or L is leucine,
Lys or K is lysine,
Met or M is methionine,
Nle is norleucine,
Phe or F is phenylalanine,
Pro or P is proline,
Ser or S is serine,
Thr or T is threonine,
Trp or W is tryptophan,
Tyr or Y is tyrosine, and
Val or V is valine.

Certain other abbreviations used herein are defined as follows:
Boc is tert-butyloxycarbonyl,
Bzl is benzyl,
DCM is dichloromethane,
DIC is N,N-diisopropylcarbodiimide,
DIEA is diisopropylethyl amine,
Dmab is 4-{N-(1-(4,4-dimethyl-2,6-dioxocyclohexylidene)-3-methylbutyl)-amino}benzyl,
DMAP is 4-(dimethylamino)pyridine,
DMF is dimethylformamide,
DNP is 2,4-dinitrophenyl,
Fmoc is Fluorenylmethyloxycarbonyl,
HBTU is 2-(1H-benzotriazole-1-yl)-1,1,3,3-tetramethyluronium hexafluorophosphate,
cHex is cyclohexyl,
HOAt is O-(7-azabenzotriazol-1-yl)-1,1,3,3-tetramethyluronium hexafluorophosphate,
HOBt is 1-hydroxy-benzotriazole,
Mmt is 4-methoxytrityl,
NM is N-methylpyrrolidone,
Pbf is 2,2,4,6,7-pentamethyldihydrobenzofuran-5-sulfonyl,
Ph is phenyl,
tBu is tert-butyl,
TIS is triisopropylsilane,
TOS is tosyl,
Trt is trityl,
TFA is trifluoro acetic acid,
TFFH is tetramethylfluoroforamidinium hexafluorophosphate, and
Z is benzyloxycarbonyl.

All abbreviations (e.g., Ala) of amino acids in this disclosure stand for the structure of —NH—C(R)(R')—CO—, wherein R and R' each is, independently, hydrogen or the side chain of an amino acid (e.g., R=$CH_3$ and R'=H, for Ala), or R and R' may be joined to form a ring system.

What is meant by "N-methyl-cysteine" (SEQ ID NO:1), "NMe-Cys", "N-MeCys" or "NMeCys", which terms are equivalents of each other, is:

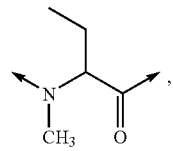

which can be in L- or D-configuration.

What is meant by "N—($C_1$-$C_5$)-cysteine" or "N—($C_1$-$C_5$)-Cys" (SEQ ID NO:1), which terms are equivalents of each other, is:

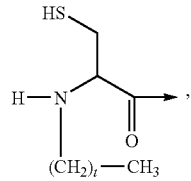

wherein t is an integer from 0 to 4, and which can be in L- or D-configuration.

What is meant by "N-methyl-thiazolidine", "NMe-Thz", "N-MeThz" or "NMeThz", which terms are equivalents of each other, is:

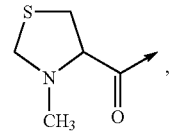

which can be in L- or D-configuration.

What is meant by "N—($C_1$-$C_5$)-thiazolidine" is:

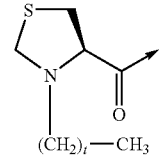

wherein t is an integer from 0 to 4, and which can be in L- or D-configuration.

What is meant by "β-(methylamino)-thioester" is:

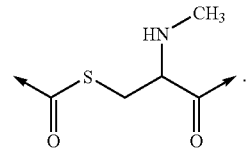

What is meant by "β-(C$_1$-C$_5$ amino)-thioester" is:

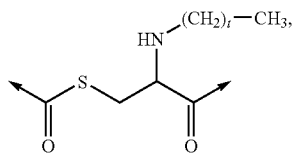

wherein t is an integer from 0 to 4.

What is meant by "S-Ph" is:

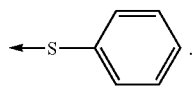

EXAMPLES

Examples are provided below to further illustrate different features of the present invention. The examples also illustrate useful methodology for practicing the invention. These examples do not limit the claimed invention.

The peptide fragments used in this invention can be prepared by standard solid phase peptide synthesis (See, e.g., Stewart, J. M. et al., Solid Phase Peptide Synthesis (Pierce Chemical Co., 2d ed. 1984)).

Example 1

Preparation of HN—MeCys-Lys-Phe-NH$_2$ (SEQ ID NO:5)

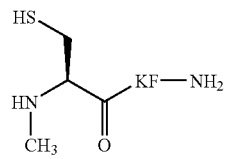

The title peptide was synthesized on a manual peptide synthesizer. Rink amide MBHA Resin (211 mg, 152 micromole, 0.72 mmole/g) (Novabiochem, San Diego, Calif., USA) was used. The Fmoc amino acids were used with the following side chain protection: Fmoc-N-MeCys(Trt)-OH (Trimen Chemicals, Lodz, Poland; (SEQ ID NO:1)), Fmoc-Lys(Boc)-OH (Novabiochem, San Diego, Calif., USA; (SEQ ID NO:2)), and Fmoc-Phe-OH (Novabiochem, San Diego, Calif., USA; (SEQ ID NO:3)). The Fmoc groups were removed by treatment with 25% piperidine in dimethylformamide (DMF) for 10 minutes, twice. In each coupling step, the Fmoc amino acid (4 equivalents), 1-hydroxybenzotriazole (HOBt) (4 equivalents), and diisopropylcarbodiimide (DIC) (4 equivalents) in N-methylpyrrolidone (NMP) were used. The following reaction cycle was used: (1) washing with DMF; (2) removing Fmoc protecting group with 25% piperidine in DMF for 20 minutes; (3) washing with DMF; and (4) coupling with pre-activated Fmoc amino acid for 60 minutes. Fmoc-N-MeCys(Trt)-OH (1.1 equivalents; (SEQ ID NO:1)) was coupled using HOBt (1.1 equivalents) and DIC (1.1 equivalents) in NMP for 12 hours. This coupling was then repeated using Fmoc-N-MeCys(Trt)-OH (0.5 equivalents; (SEQ ID NO:1)), tetramethylfluoroformamidinium hexafluorophosphate (TFFH) (0.5 equivalents), and diisopropylethylamine (DIEA) (1.0 equivalent) in NMP for one hour. During the final cycle on the synthesizer, the Fmoc was deblocked. The resulting resin was washed with DMF, dichloromethane (DCM) and methanol (MeOH) and dried under vacuum.

The resulting protected peptide-resin was deblocked and cleaved with 8% triispropylsilane (TIS)/trifluoroacetic acid (TFA) (2 ml) for 2 hours. The resin was filtered off and washed with TFA (2 ml) and DCM (2 ml). The filtrate was concentrated under nitrogen stream to less than 1 ml, which was poured into cold diethyl ether (5 ml). The precipitate formed was centrifuged and collected. The pellet was taken up in 50% aqueous acetonitrile solution and lyophilized.

This crude product was dissolved in aqueous acetonitrile and purified on a reverse-phase preparative HPLC using a Luna 5μ C$_8$(2) column (100×20 mm). The column was eluted with a linear gradient from 100% A and 0% B to 80% A and 20% B in 30 minutes, where A was 0.1% TFA in water and B was 0.1% TFA in acetonitrile. The fractions were checked by an analytical HPLC. Those containing pure product were combined and lyophilized to dryness. The purity of the compound was about 99%. 51.2 mg of the final product was obtained. ESI-MS analysis gave the molecular weight at 409.3 (in agreement with the calculated molecular weight of 409.6).

Example 2

Preparation of H-Phe-Lys-Gly-S-Ph (SEQ ID NO:6)

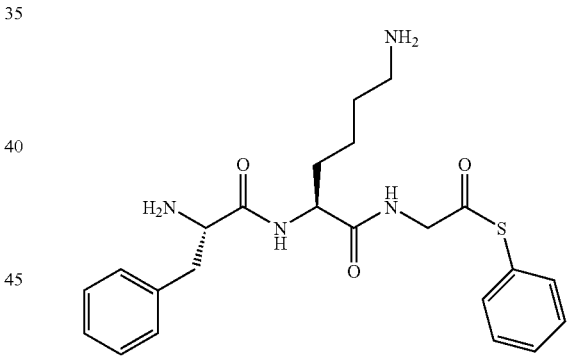

Chlorotrityl chloride resin (1.0 g, 1.49 mmole) (Novabiochem, San Diego, Calif., USA) was treated with a solution of Fmoc-Gly-OH (487 mg, 1.64 mmole; (SEQ ID NO:4)) (Novabiochem, San Diego, Calif., USA) and DIEA (770 mg, 5.96 mmole) in DCM (10 ml) for 1 hour. The resin was filtered and washed with DCM/MeOH/DIEA 17:2:1 (10 ml) twice, with DCM three times, and with DMF three times.

The Fmoc protecting group was removed by shaking the resin with 25% piperidine/DMF (10 ml) for 10 minutes and 30 minutes. The resin was then washed with DMF (10 ml) three times. Fmoc-Lys(Boc)-OH (2.79 g, 5.95 mmole; (SEQ ID NO:2)) (Novabiochem, San Diego, Calif., USA) was coupled to the resulting peptide resin by shaking with HOBt (5.95 mmole) and DIC (5.95 mmole) in NMP (10 ml) for 1 hour.

The deblocking and washing procedures were repeated as above. Boc-Phe-OH (1.58 g, 5.95 mmole; (SEQ ID NO:3)) (Bachem, Torrance, Calif., USA) was coupled to the peptide-resin by shaking with HOBt (5.95 mmole) and DIC (5.95 mmole) in NMP (10 ml) for 1 hour.

The resin was washed with DMF three times, with DCM three times, then with MeOH three times. The resin was dried under vacuum.

The protected peptide was cleaved from the resin by shaking the resin with 10 ml 1.0% TFA in DCM for 2 minutes. The resin was filtered off and the filtrate was drained into 2 ml 10% pyridine in MeOH. After the solvents were removed under vacuum, the residue was taken up in DCM, and washed with saturated NaCl twice and 1 M sodium bisulfate three times. The DCM solution was dried over sodium sulfate. The solvents were removed under vacuum to yield 120 mg of a white solid.

This protected peptide (120 mg, 218 micromole) was treated with TFFH (218 micromole) and DIEA (436 micromole) in DCM (5 ml). The resulting acid fluoride was treated with thiophenol (218 micromole) to form the thioester. After 2 hours, thin layer chromatography (TLC) eluted with 9:1 DCM/MeOH indicated that the reaction was complete. The reaction mixture was diluted with DCM (10 ml) and washed with saturated sodium bicarbonate (5 ml) three times. This solution was dried over sodium sulfate and the solvent was removed under vacuum. The resulting white solid weighed 130 mg.

This protected peptide in 2 ml of DCM was deprotected by addition of 2 ml of TFA. After 2 hours, the solvents were concentrated to 1 ml and the peptide was precipitated by the addition of 14 ml of cold diethyl ether. The resulting suspension was centrifuged and decanted. The pellet was dissolved in water and purified on a reverse-phase preparative HPLC using a Luna 5μ $C_8(2)$ column (100×20 mm). The column was eluted with a linear gradient from 100% A and 0% B to 60% A and 40% B in 30 minutes, where A was 0.1% TFA in water and B was 0.1% TFA in acetonitrile. The fractions were checked by an analytical HPLC. Those containing pure product were combined and lyophilized to dryness. 76.6 mg of the final product was obtained. ESI-MS analysis gave the molecular weight at 442.3 (in agreement with the calculated molecular weight of 442.58).

Example 3

Preparation of
H-Phe-Lys-Gly-N-MeCys-Lys-Phe-NH$_2$ (SEQ ID NO:7)

H—N-MeCys-Lys-Phe-NH$_2$ (Example 1, 5.0 mg, 12.2 micromole; (SEQ ID NO:5)) was dissolved in 200 mM, pH 8.5 phosphate/6 M guanidine buffer (0.5 ml). To it was added tris(carboxyethyl)phosphine (TCEP) (0.042 ml of 40 mg/ml solution, pH adjusted to 7). H-Phe-Lys-Gly-S-Ph (Example 2, 3.4 mg, 7.6 micromole; (SEQ ID NO:6)) was added to the resulting solution. After 40 minutes and then after 75 minutes, an additional 1.0 mg of H-Phe-Lys-Gly-S-Ph (2.2 micromole; (SEQ ID NO:6)) was added. The reaction mixture was allowed to stand at room temperature for 20 hours. Then another 1.0 mg of H-Phe-Lys-Gly-S-Ph (2.2 micromole; (SEQ ID NO:6)) was added. LC-MS analysis showed the ligation reaction was complete after 23 hour with the product of H-Phe-Lys-Gly-N-MeCys-Lys-Phe-NH$_2$ (SEQ ID NO:7), as shown by the following structure:

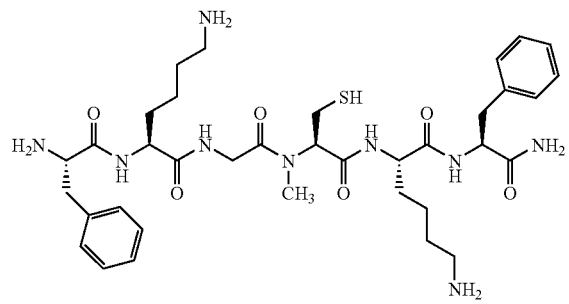 [SMILES: CN(C(=O)CNC(=O)[C@H](CCCCN)NC(=O)[C@@H](N)Cc1ccccc1)[C@@H](CS)C(=O)N[C@@H](CCCCN)C(=O)N[C@@H](Cc1ccccc1)C(N)=O]

The resulting solution was purified on a reverse-phase HPLC using a Luna 5μ $C_8(2)$ column (100×20 mm). The column was eluted with a linear gradient from 100% buffer A (0.1% TFA in water) and 0% buffer B (0.1% TFA in acetonitrile) to 60% buffer A and 40% buffer B over 30 minutes monitoring at 235 nm. 6.8 mg of the final product was obtained. ESI-MS analysis gave the molecular weight at 741.3 (in agreement with the calculated molecular weight of 741.96).

Example 4

Synthesis of N-methyl-thiazolidine-4-carboxylic acid (i.e., N-MeThz-OH)

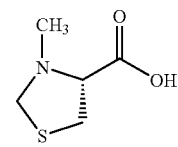

L-thiazolidine-4-carboxylic acid (13.3 g) in a mixture of 37% formaldehyde (22.5 ml) and 96% formic acid (39.3 ml) was heated to 80° C. After one hour $CO_2$ evolution ceased. The heating was continued until most of the solvent was removed. The residue was dissolved in methanol and evaporated on the rotovap three times. One equivalent of concentrated hydrochloric acid was added and the resulting salt crystallized from methanol and ethyl ether. Yield 17.0 g (92%).

Example 5

Preparation of N-methyl-thiazolidine-4-carboxylic acid-lysine-glycine-phenylthioester (i.e., N-MeThz-Lys-Gly-S-Ph) (SEQ ID NO:8)

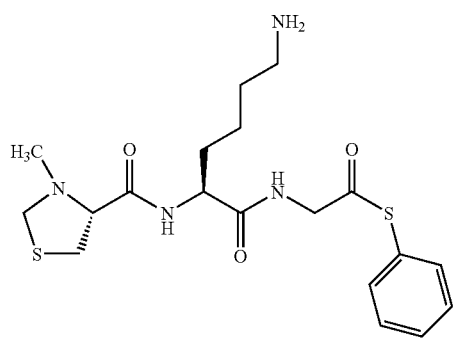 [SMILES: CN1CSC[C@H]1C(=O)N[C@@H](CCCCN)C(=O)NCC(=O)Sc1ccccc1]

Chlorotrityl chloride resin (714 mg, 1.0 mmole) (Novabiochem, San Diego, Calif., USA) was treated with a solution of Fmoc-Gly-OH (595 mg, 2.0 mmole; (SEQ ID NO:4)) (Novabiochem, San Diego, Calif., USA) and DIEA (517 mg, 4.0 mmole) in DCM (9 ml) for 2 hours. The resin was filtered and washed with DCM/MeOH/DIEA 17:2:1 (10 ml) twice, with DCM three times, and with DMF three times.

The Fmoc protecting group was removed as described above by shaking the resin with 25% piperidine/DMF (10 ml) for 10 minutes and 30 minutes. The resin was washed with DMF (10 ml) three times. Fmoc-Lys(Boc)-OH (1.87 g, 4.0 mmole; (SEQ ID NO:2)) (Novabiochem, San Diego, Calif., USA) was coupled to the resulting free amine resin by shaking with HOBt (4.0 mmole), DIEA (8.0 mmole) and HBTU (4.0 mmole) in NMP (15 ml) for 1 hour.

The deblocking and washing procedure was repeated as described above. N-methyl-thiazolidine-4-carboxylic acid (N-MeThz-OH) (Example 4, 730 mg, 4.0 mmole) was coupled to the resulting peptide-resin by shaking with HOBt (4.0 mmole), DIEA (8.0 mmole) and HBTU (4.0 mmole) in NMP (15 ml) for 1 hour.

The resin was washed with DMF three times, with DCM three times, then with MeOH three times. The resin was dried under vacuum.

The protected peptide was cleaved from the resin by shaking the resin with acetic acid (HOAc)/trifluoroethanol/DCM 2:2:6 (10 ml) for 2 hours. The resin was filtered and washed with cleavage solution (10 ml). The filtrates were combined and concentrated. The residue was dissolved in water then lyophilized.

The resulting viscous oil was purified on a silica gel flash column (Biotage 1.2×15 cm) eluted with 5% MeOH/DCM. The fractions were pooled and the solvents were removed under vacuum to yield 201 mg of the protected peptide.

This protected peptide (100 mg, 231 micromole) was treated with TFFH (231 micromole) and DIEA (462 micromole) in DCM (5 ml). The resulting acid fluoride was treated with thiophenol (231 micromole) to form the thioester. The reaction mixture was diluted with DCM (10 ml) and washed with saturated sodium bicarbonate (5 ml) three times. This solution was dried over sodium sulfate and the solvent was removed under vacuum. This protected peptide thioester in 2 ml of DCM was deprotected by addition of 2 ml of TFA. After one hour, the solvents were concentrated and the peptide precipitated by the addition of ether. The resulting suspension was centrifuged and decanted. The pellet was dissolved in water and lyophilized to yield a white solid. 45.9 mg of the final product was obtained.

An M+1 ion at 425.0 mass units was detected by ESI-MS. The calculated molecular weight is 424.6 mass units.

Example 6

Preparation of
N-MeThz-Lys-Gly-MeCys-Lys-Phe-NH$_2$ ID NO:9)

N-MeThz-Lys-Gly-S-Ph (Example 5, 1.2 mg, 2.83 micromol; (SEQ ID NO:8)) and H—N-MeCys-Lys-Phe-NH$_2$ (Example 1, 1.2 mg, 2.83 micromol; (SEQ ID NO:5)) were dissolved in 200 mM pH 8.5 phosphate/6 M guanidine buffer (0.2 ml). Tris(carboxyethyl)phosphine hydrochloride (TCEP) (0.042 ml of 40 mg/mL solution, pH adjusted to 7) was added to this solution. The reaction mixture was allowed to stand at room temperature for 4 hours. LC-MS analysis showed the ligation was complete in 4 hours and the product was N-MeThz-Lys-Gly-MeCys-Lys-Phe-NH$_2$ (SEQ ID NO:9), as shown by the following structure:

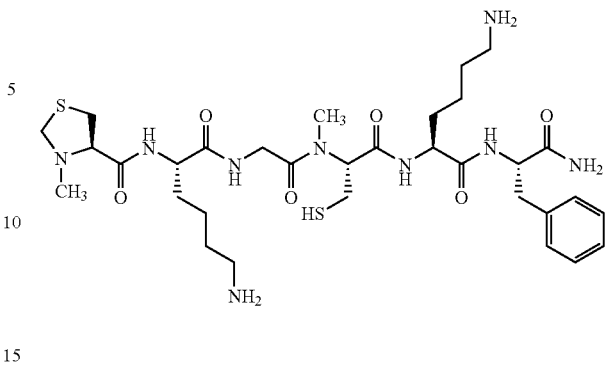

Example 7

Preparation of
N-Mecys-Lys-Gly-Mecvs-Lys-Phe-Nh(SEQ ID NO:10)

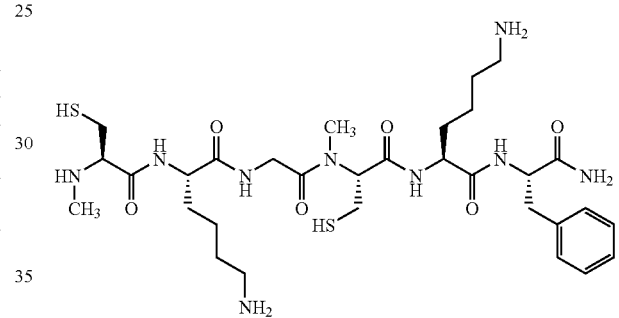

To N-MeThz-Lys-Gly-MeCys-Lys-Phe-NH$_2$ (Example 6, 2.0 mg, 2.83 micromol; (SEQ ID NO:9)) in 200 mM pH 8.5 phosphate/6 M guanidine buffer (0.2 ml) was added 0.2 M methoxyamine HCl to adjust the pH to 4.0. The reaction was monitored by using LC-MS. In 2 hours the reaction was complete. The reaction solution was stored at −20° C. overnight.

Example 8

Preparation N-MeThz-Lys-Gly-N-MeCys-Lys-Gly-MeCys-Lys-Phe-NH$_2$ (SEQ ID NO:11)

The pH of the thawed reaction mixture obtained from Example 7 was adjusted to 8 by adding 2N NaOH. To it was added N-MeThz-Lys-Gly-S-Ph (Example 5, 1.2 mg, 2.83 micromol; (SEQ ID NO:8)). The ligation was monitored by LC-MS. In 3 hours the reaction was complete.

The resulting solution was purified on reverse phase HPLC (Luna 5μ C$_8$(2) 100×4.6 mm column) eluted from 100% buffer A (0.1% TFA in water) and 0% buffer B (0.1% TFA in acetonitrile) to 50% buffer A and 50% buffer B over 15 minutes monitoring at 220 nm. An M+1 ion at 1026.6 mass units was detected by ESI-MS. The calculated molecular weight of N-MeThz-Lys-Gly-N-MeCys-Lys-Gly-MeCys-Lys-Phe-NH$_2$ (SEQ ID NO:11) is 1026.4 mass units.

What is claimed is:

1. A method for forming an amide bond between a first molecule having a thioester moiety and a second molecule having an N—($C_1$-$C_5$)-cysteine (SEQ ID NO:1) residue having an unoxidized sulfhydryl moiety, comprising the steps of:
   (a) reacting said thioester moiety of the first molecule with said unoxidized sulfhydryl moiety of the N—($C_1$-$C_5$)-cysteine (SEQ ID NO:1) residue of the second molecule to generate an intermediate connecting the first and second molecules with a β-($C_1$-$C_5$ amino)-thioester linkage; and
   (b) allowing the β-($C_1$-$C_5$ amino)-thioester linkage of the intermediate to rearrange intramolecularly to from an amide bond connecting said first and second molecules.

2. The method as recited in claim 1, wherein said N—($C_1$-$C_5$)-cysteine (SEQ ID NO:1) residue is an N-methyl-cysteine (SEQ ID NO:1) residue and wherein said β-($C_1$-$C_5$ amino)-thioester linkage is a β-(methylamino)-thioester linkage.

3. The method of claim 1, wherein said first and second molecules are independently selected from a group including peptide fragments, polypeptides, peptidomimetics and proteins.

4. The method of claim 1, wherein said reaction and rearrangement steps take place in a solution or a solid phase.

5. The method of claim 1, in which said reaction step takes place in the presence of at least one thiol catalyst.

6. The method of claim 5, wherein said thiol catalyst is selected from the group consisting of thiophenol, 1-thio-2-nitrophenol, 2-thio-benzoic acid, 2-thio-pyridine, 4-thio-2-pyridinecarboxylic acid, 4-thio-2-nitropyridine, 4-mercaptophenylacetic acid, 2-mercaptoethanesulfonic acid, 3-mercapto-1-propanesulfonic acid, and 2,3-dimercaptopropanesulphonic acid.

7. A method for synthesizing a polypeptide or a protein by ligation of two peptide fragments, comprising the steps of:
   (a) forming an amide bond by ligation of a C-terminal thioester of the first peptide fragment containing N-terminal N—($C_1$-$C_5$)-thiazolidine with an N-terminal N—($C_1$-$C_5$)-cysteine (SEQ ID NO:1) of the second peptide fragment; and
   (b) treating the ligation product with a nucleophilic agent under acidic condition to convert the N-terminal N—($C_1$-$C_5$)-thiazolidine residue to the N-terminal N—($C_1$-$C_5$)-cysteine residue (SEQ ID NO:1).

8. The method as recited in claim 7, wherein said nucleophilic agent is O-alkylhydroxylamine.

9. The method as recited in claim 8, wherein said O-alkylhydroxylamine is O-methylhydroxylamine.

10. The method according to claim 7, wherein said acidic conditions are in the range of pH 2.0 to pH 6.0.

11. The method according to claim 7, wherein said step (a) and step (b) can be repeated until a desired polypeptide or protein is formed.

12. A method for synthesizing a polypeptide containing a free N-terminal N—($C_1$-$C_5$)-cysteine (SEQ ID NO:1), comprising the steps of:
   (a) synthesizing a polypeptide containing an N-terminal N—($C_1$-$C_5$)-thiazolidine residue in solid or solution phase; and
   (b) treating the polypeptide with a nucleophilic agent under acidic condition to convert the N-terminal N—($C_1$-$C_5$)-thiazolidine residue to a free N-terminal N—($C_1$-$C_5$)-cysteine (SEQ ID NO:1) residue.

13. The method as recited in claim 12, wherein said nucleophilic agent is O-alkylhydroxylamine.

14. The method as recited in claim 13, wherein said O-alkylhydroxylamine is O-methylhydroxylamine.

15. A method for synthesizing N—($C_1$-$C_5$)-thiazolidine-carboxylic acid, comprising the steps of:
   (a) treating L-thiazolidine-4-carboxylic acid with an aldehyde in the presence of an acid; and
   (b) purifying the product.

16. A method as recited in claim 15, wherein said aldehyde is formaldehyde.

17. A method as recited in claim 15, wherein said acid is formic acid.

18. A method for synthesizing a polypeptide thioester, comprising the steps of:
   (a) synthesizing a peptide in which N-terminal amino group is protected with a protecting group and C-terminal carboxylic acid functional group is free;
   (b) converting a peptide in which N-terminal amino group is protected with a protecting group and C-terminal carboxylic acid functional group is free to a peptide in which N-terminal amino group is protected with a protecting group and C-terminal functional group is acid fluoride;
   (c) converting a peptide in which N-terminal amino group is protected with a protecting group and C-terminal functional group is acid fluoride to a peptide in which N-terminal amino group is protected with a protecting group and C-terminal functional group is thioester; and
   (d) deprotecting a peptide in which N-terminal amino group is protected with a protecting group and C-terminal functional group is thioester to generate a free peptide containing a thioester functional group at the C-terminus.

19. A method for synthesizing a polypeptide thioester, comprising the steps of:
   (a) synthesizing a peptide in which side-chain functional group(s) and N-terminal amino group are protected with protecting groups and the C-terminal carboxylic acid functional group is free;
   (b) converting a peptide in which side-chain functional group(s) and N-terminal amino group are protected with protecting groups and the C-terminal carboxylic acid functional group is free to a peptide in which side-chain functional group(s) and N-terminal amino group are protected with protecting groups and the C-terminal functional group is acid fluoride;

(c) converting a peptide in which side-chain functional group(s) and N-terminal amino group are protected with protecting groups and the C-terminal functional group is acid fluoride to a peptide in which side-chain functional group(s) and N-terminal amino group are protected with protecting groups and the C-terminal functional group is thioester; and (d) deprotecting a peptide in which side-chain functional group(s) and N-terminal amino group are protected with protecting groups and the C-terminal functional group is thioester to generate a free peptide containing a thioester functional group at the C-terminus.

* * * * *

SEQUENCE LISTING

<160> NUMBER OF SEQ ID NOS: 11

<210> SEQ ID NO 1
<211> LENGTH: 1
<212> TYPE: PRT
<213> ORGANISM: Artificial Sequence
<220> FEATURE:
<223> OTHER INFORMATION: Intermediate for chemical synthesis of
      polypeptides and proteins
<220> FEATURE:
<221> NAME/KEY: MISC_FEATURE
<222> LOCATION: (1)..(1)
<223> OTHER INFORMATION: Xaa = N-methylcysteine (N-MeCys), N-(C1-C5)-
      cysteine (N-(C1-C5)-Cys), or fluorenylmethyloxycarbonyl N-
      methylcysteine trityl hydroxide (Fmoc-N-MECys(Trt)-OH)

<400> SEQUENCE: 1

Xaa
1

<210> SEQ ID NO 2
<211> LENGTH: 1
<212> TYPE: PRT
<213> ORGANISM: Artificial Sequence
<220> FEATURE:
<223> OTHER INFORMATION: Intermediate for chemical synthesis of
      polypeptides and proteins
<220> FEATURE:
<221> NAME/KEY: MISC_FEATURE
<222> LOCATION: (1)..(1)
<223> OTHER INFORMATION: Xaa = fluorenylmethyloxycarbonyl lysine tert-
      butyloxycarbonyl hydroxide (Fmoc-Lys(Boc)-OH)

<400> SEQUENCE: 2

Xaa
1

<210> SEQ ID NO 3
<211> LENGTH: 1
<212> TYPE: PRT
<213> ORGANISM: Artificial Sequence
<220> FEATURE:
<223> OTHER INFORMATION: Intermediate for chemical synthesis of
      polypeptides and proteins
<220> FEATURE:
<221> NAME/KEY: MISC_FEATURE
<222> LOCATION: (1)..(1)
<223> OTHER INFORMATION: Xaa = fluorenylmethyloxycarbonyl phenylalanine
      hydroxide (Fmoc-Phe-OH) or tert-butyloxycarbonyl phenylalanine
      hydroxide (Boc-Phe-OH)

<400> SEQUENCE: 3

Xaa
1

<210> SEQ ID NO 4
<211> LENGTH: 1
<212> TYPE: PRT
<213> ORGANISM: Artificial Sequence
<220> FEATURE:
<223> OTHER INFORMATION: Intermediate for chemical synthesis of
      polypeptides and proteins
<220> FEATURE:
<221> NAME/KEY: MISC_FEATURE
<222> LOCATION: (1)..(1)
<223> OTHER INFORMATION: Xaa = fluorenylmethyloxycarbonyl glycine
      hydroxide (Fmoc-Gly-OH)

<400> SEQUENCE: 4

Xaa

```
<210> SEQ ID NO 5
<211> LENGTH: 3
<212> TYPE: PRT
<213> ORGANISM: Artificial Sequence
<220> FEATURE:
<223> OTHER INFORMATION: Intermediate for chemical synthesis of
      polypeptides and proteins
<220> FEATURE:
<221> NAME/KEY: MISC_FEATURE
<222> LOCATION: (1)..(1)
<223> OTHER INFORMATION: Xaa = N-methylcysteine (H-N-MeCys)
<220> FEATURE:
<221> NAME/KEY: MOD_RES
<222> LOCATION: (3)..(3)
<223> OTHER INFORMATION: AMIDATION

<400> SEQUENCE: 5

Xaa Lys Phe
1

<210> SEQ ID NO 6
<211> LENGTH: 3
<212> TYPE: PRT
<213> ORGANISM: Artificial Sequence
<220> FEATURE:
<223> OTHER INFORMATION: Intermediate for chemical synthesis of
      polypeptides and proteins
<220> FEATURE:
<221> NAME/KEY: MISC_FEATURE
<222> LOCATION: (3)..(3)
<223> OTHER INFORMATION: Xaa = glycine phenylthioester (Gly-S-Ph)

<400> SEQUENCE: 6

Phe Lys Xaa
1

<210> SEQ ID NO 7
<211> LENGTH: 6
<212> TYPE: PRT
<213> ORGANISM: Artificial Sequence
<220> FEATURE:
<223> OTHER INFORMATION: Intermediate for chemical synthesis of
      polypeptides and proteins
<220> FEATURE:
<221> NAME/KEY: MISC_FEATURE
<222> LOCATION: (4)..(4)
<223> OTHER INFORMATION: Xaa = N-methylcysteine (N-MeCys)
<220> FEATURE:
<221> NAME/KEY: MOD_RES
<222> LOCATION: (6)..(6)
<223> OTHER INFORMATION: AMIDATION

<400> SEQUENCE: 7

Phe Lys Gly Xaa Lys Phe
1               5

<210> SEQ ID NO 8
<211> LENGTH: 2
<212> TYPE: PRT
<213> ORGANISM: Artificial Sequence
<220> FEATURE:
<223> OTHER INFORMATION: Intermediate for chemical synthesis of
      polypeptides and proteins
<220> FEATURE:
<221> NAME/KEY: MISC_FEATURE
<222> LOCATION: (1)..(1)
<223> OTHER INFORMATION: Xaa = N-methyl-thiazolidine-4-carboxylic acid-
      lysine (N-MeThz-Lys)
<220> FEATURE:
<221> NAME/KEY: MISC_FEATURE
<222> LOCATION: (2)..(2)
```

-continued

<223> OTHER INFORMATION: Xaa = glycine phenylthioester (Gly-S-Ph)

<400> SEQUENCE: 8

Xaa Xaa
1

<210> SEQ ID NO 9
<211> LENGTH: 5
<212> TYPE: PRT
<213> ORGANISM: Artificial Sequence
<220> FEATURE:
<223> OTHER INFORMATION: Intermediate for chemical synthesis of
      polypeptides and proteins
<220> FEATURE:
<221> NAME/KEY: MISC_FEATURE
<222> LOCATION: (1)..(1)
<223> OTHER INFORMATION: Xaa = N-methyl-thiazolidine-4-carboxylic acid-
      lysine (N-MeThz-Lys)
<220> FEATURE:
<221> NAME/KEY: MISC_FEATURE
<222> LOCATION: (3)..(3)
<223> OTHER INFORMATION: Xaa = methyl-cysteine (MeCys)
<220> FEATURE:
<221> NAME/KEY: MOD_RES
<222> LOCATION: (5)..(5)
<223> OTHER INFORMATION: AMIDATION

<400> SEQUENCE: 9

Xaa Gly Xaa Lys Phe
1               5

<210> SEQ ID NO 10
<211> LENGTH: 6
<212> TYPE: PRT
<213> ORGANISM: Artificial Sequence
<220> FEATURE:
<223> OTHER INFORMATION: Intermediate for chemical synthesis of
      polypeptides and proteins
<220> FEATURE:
<221> NAME/KEY: MISC_FEATURE
<222> LOCATION: (1)..(1)
<223> OTHER INFORMATION: Xaa = N-methyl-cysteine (N-MeCys)
<220> FEATURE:
<221> NAME/KEY: MISC_FEATURE
<222> LOCATION: (4)..(4)
<223> OTHER INFORMATION: Xaa = methyl-cysteine (MeCys)
<220> FEATURE:
<221> NAME/KEY: MOD_RES
<222> LOCATION: (6)..(6)
<223> OTHER INFORMATION: AMIDATION

<400> SEQUENCE: 10

Xaa Lys Gly Xaa Lys Phe
1               5

<210> SEQ ID NO 11
<211> LENGTH: 8
<212> TYPE: PRT
<213> ORGANISM: Artificial Sequence
<220> FEATURE:
<223> OTHER INFORMATION: Intermediate for chemical synthesis of
      polypeptides and proteins
<220> FEATURE:
<221> NAME/KEY: MISC_FEATURE
<222> LOCATION: (1)..(1)
<223> OTHER INFORMATION: Xaa = N-methyl-thiazolidine-4-carboxylic acid-
      lysine (N-MeThz-Lys)
<220> FEATURE:
<221> NAME/KEY: MISC_FEATURE
<222> LOCATION: (3)..(3)
<223> OTHER INFORMATION: Xaa = N-methyl-cysteine (N-MeCys)
<220> FEATURE:
<221> NAME/KEY: MISC_FEATURE
<222> LOCATION: (6)..(6)

```
<223> OTHER INFORMATION: Xaa = methyl-cysteine (MeCys)
<220> FEATURE:
<221> NAME/KEY: MOD_RES
<222> LOCATION: (8)..(8)
<223> OTHER INFORMATION: AMIDATION

<400> SEQUENCE: 11

Xaa Gly Xaa Lys Gly Xaa Lys Phe
1               5
```